United States Patent [19]

Cashell et al.

[11] Patent Number: 4,860,224

[45] Date of Patent: Aug. 22, 1989

[54] SURFACE ANALYSIS SPECTROSCOPY APPARATUS

[75] Inventors: Edmund M. Cashell; Liam McDonnell, both of Cork, Ireland

[73] Assignee: 501 Tekscan Limited, Dublin, Ireland

[21] Appl. No.: 866,062

[22] Filed: May 21, 1986

[30] Foreign Application Priority Data

May 22, 1985 [IE] Ireland ................................ 1278/85

[51] Int. Cl.⁴ .......................................... G01N 23/00
[52] U.S. Cl. .............................. 364/551.01; 250/309; 250/311; 250/441.1; 250/442.1; 250/443.1
[58] Field of Search ............ 250/309, 311, 341, 441.1, 250/442.1, 443.1; 364/551, 551.01; 374/5, 46

[56] References Cited

U.S. PATENT DOCUMENTS

| | | | |
|---|---|---|---|
| 3,878,392 | 4/1975 | Yew et al. | 250/309 X |
| 3,914,606 | 10/1975 | Hashimoto et al. | 250/305 |
| 3,935,453 | 1/1976 | Liebl | 250/292 |
| 3,949,221 | 4/1976 | Liebl | 250/281 |
| 4,218,617 | 8/1980 | Cazaux | 250/305 |
| 4,296,323 | 10/1981 | Gerlach | 250/309 X |
| 4,334,844 | 6/1982 | Tanaka | 250/311 X |
| 4,378,701 | 4/1983 | Mountain et al. | 374/47 X |
| 4,439,049 | 3/1984 | Hoogendoorn et al. | 374/5 X |
| 4,564,758 | 1/1986 | Slodzian et al. | 250/309 |
| 4,567,767 | 2/1986 | Quate et al. | 73/606 |
| 4,578,584 | 3/1986 | Baumann et al. | 250/341 |
| 4,593,196 | 6/1986 | Yates | 250/305 |
| 4,628,468 | 12/1986 | Thompson et al. | 364/556 |
| 4,680,467 | 7/1987 | Bryson, III et al. | 250/309 X |
| 4,687,930 | 8/1987 | Tamura et al. | 250/309 |
| 4,694,170 | 9/1987 | Slodzian et al. | 250/309 |

FOREIGN PATENT DOCUMENTS 0057290 8/1982 European Pat. Off. .
2221729 3/1974 France .
WO79/01156 12/1979 World Int. Prop. O. .

OTHER PUBLICATIONS

*Chemical Analysis of Surfaces by Total-Reflection-Angle X-Ray Spectroscopy in RHEED Experiments (RHEED-TRAXS)*, Hasegawa, S.; Ino, S; Yamamoto, Y.; Daimon, M. Japanese Journal of Applied Physics, vol. 24, No. 6, Jun. 1985, pp. L387-L390.

*Energy Spectra of Thermally Stimulated Exoelectrons from KCl:Tl X-Irradiated at 77K*, Kamada, M.; Yoshiara, K.; Tsutsumi, K.; Japanese Journal of Applied Physics, vol. 23, Mar. 1984, pp. 286-290.

*Reduction of the Bremsstrahlung Background in the Proton-Induced X-Ray Emission Analysis of Insulating Samples*, Mingay, D. W.; Barnard, E., Nuclear Instruments & Methods, vol. 157, No. 3, (1978, 12).

*Combined Ion, Electron, and X-Ray Beams for Studies of Surfaces and Thin Films*, Musket, R. G., Nuclear Instruments and Methods, 144(1977), pp. 241-246.

*An Ultrahigh Vacuum Electron Spectrometer for Surface Studies*, Brundle, C. R.; Roberts, M. W., Journal of Electron Spectroscopy and Related Phenomena, 3(1974), pp. 241-261.

*L'Imagerie Thermique Ou l'art et la Maniere de <<Voir les Temperatures>>*, Dossiers Techniques Instrumentation, 2045 Electronique Industrielle, (1983), Auril, No. 50, Paris, France, (Translation Enc.).

Primary Examiner—Parshotam S. Lall
Assistant Examiner—Edward R. Cosimano
Attorney, Agent, or Firm—Wolf, Greenfield & Sacks

[57] ABSTRACT

In an apparatus for surface analysis microscopy, a number of analysis device are mounted on an ultra-high vacuum chamber. The devices include a beam source of locally heating a selected region of a specimen and a temperature-detector for monitoring the heating of the selected region, as well as an electron gun and an analyzer for detecting emission from a specimen region subjected to electron bombardment. An ion gun may also be provided. The apparatus enables thermal microscopy of a specimen to be carried out in conjunction with other surface analysis techniques including, inter alia, scanning electron microscopy and Auger electron microscopy, within a single apparatus and during a single experimental operation. A novel configuration of cylindrical mirror analyser facilitates mounting a multiplicity of analysis devices on the chamber in a compact manner for studying a specimen at a single position.

19 Claims, 5 Drawing Sheets

SURFACE ANALYSIS SPECTROSCOPY APPARATUS

BACKGROUND OF THE INVENTION

1. Field of the Invention

This invention relates to apparatus and methods for surface analysis. Surface analysis is concerned with the determination of the elemental and chemical composition of the uppermost atomic layers of a material or component, together with the microstructural and physical properties in the vicinity of the surface and the actual surface configuration.

2. Description of the prior art

In recent years, surface sensitive analytical techniques have found increasing application in materials science and technology. Corrosion, catalysis and wear are just a few of the many surface/interface-specific materials phenomena for which bulk sampling analytical techniques, e.g. the X-ray microprobe analyser, are either ineffective or inappropriate. The most important requirement for a surface technique is the provision of an ultra-high vacuum environment in which a given surface condition can be established and maintained.

An array of surface sensitive techniques—AES, XPS, SIMS, PAS, SAM and SEM, as discussed below—are available to probe the physico/chemical characteristics of surfaces and interfaces. An outline of the nature and capabilities of each of these techniques follows.

Auger electron spectroscopy (AES) is a well established surface analytical technique which enables the chemical composition of solid surfaces to be qualitatively determined and, with calibration, quantitatively determined. Being a surface technique, AES requires the presentation or creation of a solid surface within an ultra-high vacuum, for example by fracture or ion beam erosion. This mandatory experimental environment keeps even the most reactive surfaces chemically stable for the duration of an analysis.

In AES, an electron beam is used to probe the surface and generate the Auger spectra. By using small electron beam diameters (approximately $1\mu$) and rastered beams, high resolution scanning Auger microscopy (SAM) maps of lateral elemental distributions can be generated. Sensitive to all elements except hydrogen and helium, AES samples only the top two or three layers of a surface. The addition of ion beam erosion enables elemental depth profiles into the bulk to be determined, but this necessarily involves destruction and removal of the surface layers in the region under study.

X-ray photoelectron spectroscopy (XPS), secondary ion mass spectroscopy (SIMS), and scanning electron microscopy (SEM) also each involve the bombardment of a surface located in a high or ultra-high vacuum environment with either a photon flux, an ion beam, or an electron beam, as appropriate, so that electrons or ions are emitted.

The physical and chemical characteristics of the surface of the sample under examination may then be established from analysis of the energies and masses of the emitted particles, which are characteristic of their origin. Three-dimensional data as to the distribution of the elements may be achieved by a combination of operations, the ion or electron beam being first of all scanned or rastered over the region of the surface to establish the two-dimensional distribution, followed by controlled sputtering of the material by an ion beam to provide elemental and chemical information on the variation in the composition of the sample with depth.

Photoacoustic or thermal spectroscopy (PAS) makes use of a phenomenon which arises when intensity-modulated electromagnetic radiation, e.g. light, is absorbed by a sample of material, thus exciting energy levels within it. De-excitation of these levels occurs for the most part by means of a non-radiative or heat-producing process. Hence the absorption of intensity-modulated electromagnetic radiation at any point in the sample results in a periodic localised heating of the material. Photoacoustic studies performed on gaseous and powdered material generally involve the use of a microphone, which detects pressure fluctuations or acoustic waves arising out of the periodic pressure rise either in the gas under study or in gas heated by proximity to the sample of powdered material under test, as appropriate.

Photoacoustic spectroscopy may also provide a non-destructive method for evaluating the optical and thermal properties of opaque and other solids. When energy from a modulated light or particle beam is absorbed by a solid sample, localised heating occurs which generates an elastic stress that propagates through the sample as an acoustic signal at the modulation frequency. This signal is a complex quantity whose magnitude and phase depend on the absorption and thermal characteristics of the sample. In circumstances where the signal does not saturate, it is related to the absorption coefficient so that the photoacoustic spectrum that results corresponds to the conventional absorption spectrum of the material of the sample. A particular advantage of PAS over other techniques is that because the detected signal depends only on light that is absorbed, scattered or transmitted light is not normally a problem.

Thus, PAS may be used to great advantage in the study of absorbed and chemisorbed molecules on surfaces, provided that the substrate itself is either non-absorbing or highly reflecting over the wavelength range. Infra-red absorption is particularly useful because the fine-structure associated with the infra-red spectra provides a sensitive probe for chemical identification and quantification. A tunable $CO_2$ laser operating between $9\mu$ and $11\mu$ at power levels of 0.1–1 W has been used, for instance, to detect submonolayer coverage of absorbed species on silver surfaces.

Detection of the photoacoustic signal in solids may be achieved by placing a piezoelectric transducer in intimate contact with the sample; these devices are sensitive to temperature changes of $10^{-7}$K and, unlike gas-microphone detection methodologies, may be made UHV compatible.

Each of the various surface sensitive analysis techniques discussed above has individual special features which render it particularly appropriate to some specific aspect of surface analysis. For example, SIMS facilitates detection of elements present in very minute quantities, while others of the techniques are preferred for picturing topographical details at high resolution or for providing chemical information as to the composition of samples sensitive to damage by particular forms of beam bombardment. A common approach nowadays is to combine a number of these techniques into a simultaneous experimental study. This procedure helps to unravel synergistic property relationships and to deconvolute artefacts arising from individual techniques.

Many surface studies are, however, hindered by the absence of a complementary technique for providing microstructural and other physical properties of the sub-surface without destroying the surface or interface in question, as occurs with sputtering or erosion. Such information, important in its own right, would provide, together with the surface data, a more complete characterisation of surface/interface behaviour.

Pulsed thermal microscopy may be used for surface and sub-surface imaging of the physical integrity of solids. In one version, a technique generally referred to as thermal wave microscopy (TWM), which is a recent development of the older technique of PAS, microscopic and macroscopic features on and beneath the surface of a sample may be detected and imaged non-destructively. The modulated thermal disturbance that occurs within the absorbing volume of a solid sample in PAS and other techniques propagates outwards as a critically damped evanescent thermal wave whose range is of the order of the thermal diffusion length. By rastering a focussed energy probe (laser, electron, ion) across the sample surface, thermal wave images at selected depths within the sample may be obtained. Image contrast results from reflection and scattering interactions of the thermal waves with mechanical and crystallographic artefacts within the image field. Thus, thermal wave microscopy may be used to locate micron scale flaws, crystallographic grain heterostructure and other thermally sensitive features of solid surfaces and subsurfaces.

The resolution, in some circumstances, depends on the thermal wavelength, which in turn is determined by the modulation frequency; the use of megahertz frequencies, with appropriate probe diameters and detector response times, optimises the spatial resolution in these cases to better than $1\mu$. While adjustment of the signal phase provides selective examination of thermal features at various depths within the image field, full-range depth profiling leading to three-dimensional image reconstruction requires the image field depth itself to be adjusted by varying the modulation frequency.

It may be noted that the term "thermal wave microscopy", as used herein and as explained in the foregoing paragraph, represents a current theory which satisfactorily explains the phenomena observed when a pulsed energy input is applied to a sample of a material. Thus while the phenomena in question are detectable and capable of analysis on the assumption that the pulsed energy input results in the establishment of thermal waves within the material of the sample, it is not necessarily the case that the effect observed may not also be explained, either for all or some of said phenomena, in terms of a different form of behaviour of the material under localised pulsed excitation by an energy input. The difficulties in determining and explaining the behaviour of materials when dealing with very thin layers having thicknesses of the order of only a small number of atoms are well known to those skilled in this art, and the necessity to proceed on the basis of theoretical explanations of the behavioural phenomena which are not necessarily definitive or correct in all experimental circumstances is also well known. Thus the term "thermal wave microscopy" is to be understood in the present text in the context of the foregoing remarks and as representing, in essence, a conceptual explanation of thermal microscopy in which a pulsed energy input is applied to a sample.

BRIEF SUMMARY OF THE INVENTION

It is an object of the invention to provide surface analysis apparatus which will facilitate, within the compass of a single ultra-high vacuum instrument, the application of both thermal wave microscopic analysis and at least one beam bombardment technique, such as SEM or Auger electron spectroscopy, to a single specimen, while also optionally allowing the addition of further analytical techniques, such as XPS, SIMS, PAS, SAM and SEM, as required.

According to a first aspect of the invention, there is provided surface analysis apparatus comprising:

(a) a substantially hermetically sealable chamber, (b) means for establishing an ultra-high vacuum environment in said chamber, (c) means for supporting a said specimen within said chamber when ultra-high vacuum conditions prevail therein, (d) at least one means for directing a beam at a selected surface region of a said specimen so that energy may be transferred to said surface region, (e) means for detecting emissions from a said surface region when excited by said energy transfer, said detecting means including means for establishing the temperature of said surface region, and (f) means for analysing said emissions to provide data indicative of at least surface properties of the specimen.

Said beam-directing means may include means for modulating the intensity of said beam. Said means for directing a beam at a selected surface region of a said specimen may be an electron gun, an ion gun or a laser. In each case, said means incorporates or is associated with means for focussing said beam onto a said selected surface region and the apparatus may comprise or be associated with means for scanning or rastering said beam relative to the surface of a sample to be studied according to a predetermined pattern.

Said means for establishing the temperature of a surface region to which energy is being transferred by the directing of a beam onto it may include an infra-red detector for sensing the heat emission from said surface region. Alternatively a capacitance probe may be positioned close to the specimen for detecting the expansion of the specimen when heated by said energy transfer to a said surface region and thereby providing an indication of the extent of the heating. In a further arrangement, a piezo-electric crystal may be attached to the specimen and the acoustic waves resulting from the thermoacoustic effect on heating the particular local surface area of the sample detected, to provide yet another variety of temperature indication. In each case, ancillary features of said means include associated apparatus for transforming the primary information yielded by the probe or transducer into a temperature reading meaningful to the user.

Said emission detecting means may further include either a cylindrical mirror analyser (CMA) or a concentric hemispherical analyser (CHA) or both. Thus in a preferred construction of the apparatus of the invention in which either a CMA or a CHA or both are provided, not only thermal emission but also particle emission may be detected and analysed, as well as which optical emission may be sensed.

In an especially favoured construction of the apparatus of the invention, the chamber may have a generally spherical region in which a number of narrow-angle ports permit, inter alia, an infra-red thermal emission detector and a concentric hemispherical analyser to be mounted so as to substantially cluster about a specimen position. A primary radiation source such as an electron or ion gun may also be included in the cluster of features focussing on said specimen position, and a cylindrical mirror analyser may also be port-mounted so that its main or longitudinal axis may also pass substantially through said specimen position. Alternatively a CMA may be mounted on a further port so that it is aligned along an alternative axis to focus on a second specimen position displaced from that around which the narrow-angle-port-mounted analysis means are arranged, and a specimen may be transferred between said positions during analysis by suitable means, or alternatively two specimens may be handled, one at each position. The axis of said CMA then passes substantially through said second specimen position.

The apparatus may form part of a system in which computer means are used to handle the data yielded by the detectors to correlate it with the scanning of the specimen and to provide output results in a form meaningful to the user. Said computer means may correlate data from said detecting means with said scanning or rastering of the specimen. Said computer may further control a plurality of said beam-directing means, to activate selected ones of said plurality of beam-directing means in dependence on the presence of certain predetermined characteristics in said emissions from said surface region. A system of this kind may be optionally semi- or fully automated in accordance with the particular requirements of each installation, for monitoring signals derived from the sensing or measuring of said surface region temperatures.

The apparatus may also include means for introducing a test specimen into said chamber when ultra-high vacuum conditions prevail therein, as well as means for mounting and manipulating a said specimen within said chamber when ultra-high vacuum conditions prevail therein.

In a second aspect the present invention also provides a cylindrical mirror analyser comprising at least one source of primary radiation, means for focussing said radiation substantially at a specimen position located substantially on the longitudinal axis of the analyser, and means for permitting a beam source, such as a laser, to be focussed at said specimen position. Said means for permitting focussing of a beam source substantially at the specimen position may include a passage extending along the analyser to a port through which a beam from said source may be directed. Said specimen position may be located at one axial end of the analyser and said passage may be a wholly axial passage, extending to a port substantially at the axial end of the apparatus remote from that at which the specimen position is located.

Said source of primary radiation may initiate radiation along an axis disposed at substantially 90° to said longitudinal axis of the analyser, said radiation being diverted onto said longitudinal axis for focussing substantially at said specimen position. Alternatively said source of primary radiation may initiate radiation substantially along said longitudinal axis and a beam from said beam source may be diverted onto said axis by reflecting means such as a mirror displaceable between a disposition straddling said axis and a disposition in which the entirety of the mirror is clear of said axis. Said beam source may be a light source.

The beam bombardment means and the heating means and their associated monitoring, detecting and analysis means may be arranged so that when, for example, the thermal microscopy aspect of the apparatus is used to identify regions of inhomogeneity on or beneath the sample surface, surface analytical beam bombardment techniques coupled with localised ion etching may then be applied selectively to these regions of interest to elucidate their chemistry and effect a comparison with the chemistry of an equivalent control region defined elsewhere in the sample. The particular advantage of this sequence of investigations is that unusual surface and subsurface features may be examined rapidly without widespread etching and destruction of the specimen.

Alternatively, where the beam bombardment technique reveals a particular anomaly or feature of possible potential interest at a particular location of the surface of the specimen under examination, the thermal microscopy aspect of the apparatus may be brought into play to further explore and elucidate the features of the local surface and sub-surface region in question. The particular advantage of this sequence of investigations is that unusual surface features may be further examined without entailing destruction of the specimen.

Because the spatial resolution requirements, electron beam currents/optical source intensities, physical geometries and other experimental features of AES in particular and those of thermal wave microscopy are compatible, these techniques may be simultaneously incorporated into the ultra-high vacuum chamber of the apparatus of the invention, but specimen handling and in situ treatment may represent a constraint in situations where the TWM uses PAS monitoring methods and a piezoelectric transducer (PZT) must be coupled to the specimen. Accordingly, the preferred embodiments of the three detection schemes described herein are those that do not introduce such constraints.

In another aspect, the present invention also provides a surface analysis method comprising the steps of:

(a) supporting a test specimen within a substantially hermetically sealable chamber when ultra-high vacuum conditions prevail therein, (b) directing a beam at a selected surface region of said specimen so that energy may be transferred to said surface region, (c) detecting emissions from said surface region when excited by said energy transfer, and (d) analysing said emissions to provide data indicative of at least surface properties of the specimen, said emission-detecting step including establishing the temperature of said surface region.

Said beam may be modulated to apply a pulsed chopped intensity-modulated energy input to said surface region, while a further beam may be directed at said selected surface region of said specimen in the presence of certain predetermined characteristics in said emissions from said surface region.

In a particular variant of the method of the invention, the direction of a said beam at a said surface region may result in heating of said region. The method also encompasses the introduction of a said test specimen into said chamber while ultra-high vacuum conditions prevail therein.

The microscope according to the invention uses, inter alia, scanning electron and laser beams incident on a sample surface, in conditions of ultra-high vacuum, to probe physical and chemical properties of the surface and sub-surface. Because many technologically important processes—such as corrosion, wear, catalysis, microelectronic device fabrication and operation—depend on surface and near-surface rather than bulk properties of materials, a wide array of surface analysis techniques are employable. These techniques are essentially directed towards resolving the questions:
what is on or within a surface?
how much is there?
where exactly is it located?

The potential applications of the apparatus and method of the invention may be illustrated by the following examples:

Fracture

Thermal wave microscopy of a sample fractured in ultra-high vacuum may reveal alternative fracture paths in the sub-surface. These paths do not fracture to completion because of physical and chemical differences between the material at the termini of such paths and the material at the full fracture interface. Once located by thermal wave microscopy, these termini may be exposed by ion etching and then analysed by the other technique(s) in order to identify the mechanism responsible for crack termination.

Tribology

Scribing a surface in ultra-high vacuum and chemically analysing the scratch region and the debris removed from the surface is a standard technique in tribology. A complementary thermal image would provide much needed microstructural information about the underlying material. One particularly valuable advantage here is that, in this system, real engineering sample surfaces can be used rather than chemically and mechanically prepared test surfaces.

Microelectronics

Integrated microelectronics circuits may be examined by thermal wave microscopy to locate, inter-alia, delamination of sub-surface metallic coatings, microcracks within the silicon substrate, or other mechanical defects. The beam bombardment techniques are then applied in conditions of ultra-high vacuum to chemically analyse these fault regions and compare their chemistry to equivalent control regions within the microelectronic device. In this way, important information as to the basis and cause of the flaw may be provided.

An UHV environment is needed so as to be able to create and maintain a well defined surface. Inadequate vacua would contaminate the surfaces and render any analysis void. At atmospheric pressure, fresh surfaces would be contaminated in fractions of a second. Even in high vacuum, metals only remain clean for a few seconds. In UHV, even the most reactive surfaces are stable for only a few hours, and it is the ability to examine specimens by means of a multiplicity of analysis techniques under such conditions that is a particular feature of the present invention.

BRIEF DESCRIPTION OF THE DRAWINGS

Embodiments of the invention will now be described having regard to the accompanying drawings in which.

DETAILED DESCRIPTION OF THE PREFERRED EMBODIMENTS

Figure 1:
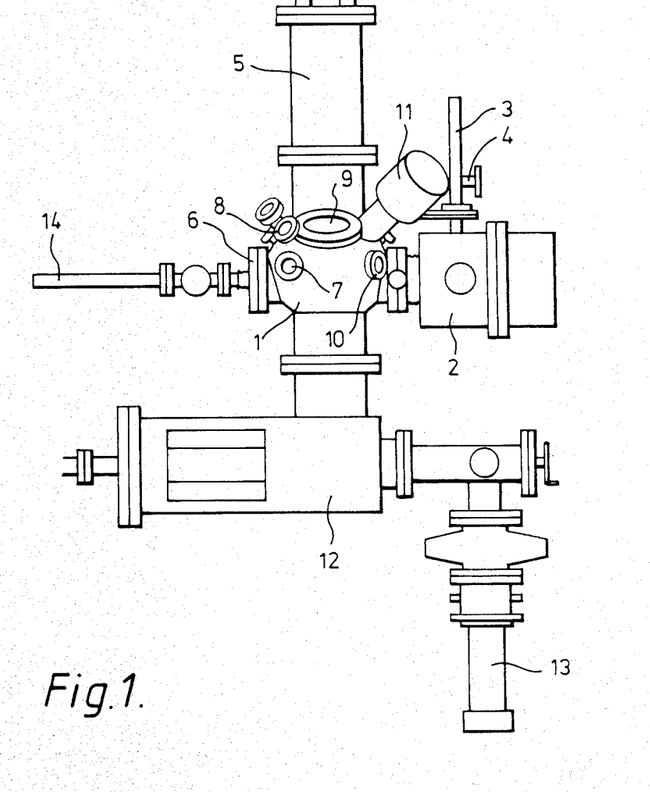
FIG. 1 is a schematic diagram of a first embodiment of surface analysis microscopy apparatus according to the invention.

As shown in FIG. 1, the surface analysis apparatus according to the invention includes a generally spherical analytical chamber 1, a specimen preparation chamber 2 and a specimen interlock 3 isolated by gate valves such as 4. In order to permit a high throughput of a range of specimens, the system preferably has a number of preparation facilities including heating, cooling, fracture and ion beam erosion, all of which may be carried out within the UHV environment. AES is performed using a cylindrical mirror analyser 5, mounted on an upwardly opening port on the top of the chamber 1, with its axis disposed substantially vertically.

The generally spherical analytical chamber 1 is provided with a number of further ports 6 to 10 centred on the specimen position during analysis, which, in this embodiment of the apparatus, will be substantially at the centre of the chamber. Still further ports provide access for a sub-micron gun 11 and a laser (not indicated in this drawing), while some of ports 6 to 10 are available as required for the addition of further techniques such as XPS and SIMS.

Evacuation of the chamber 1 takes place by the action of a primary pumping chamber 12 and secondary pumping means indicated by reference 13. A manipulator 14 allows ready adjustment of specimen position and orientation for the different aspects of the test techniques.

A particular feature of the apparatus of the present invention is its ability to enable both pulsed thermal microscopy and surface analytical techniques such as AES to be applied to a single specimen, all within the confines of a single experimental unit, the interior of which is maintained under UHV during both phases or aspects of the investigation. The pulsed thermal microscopy, in particular, TWM, and the surface analysis technique or techniques employed may be carried on either sequentially or simultaneously, depending on the nature of the investigations to be carried out, e.g.

whether they relate to a production situation or whether they represent laboratory type experiments. Thus non-destructive testing of a selected surface region may be particularly facilitated, while the testing may nonetheless be carried out in a reasonably short period of time, and yet within a UHV environment.

The apparatus of the invention may be employed with any of three methods of detection in TWM. In the first case, piezo-electric detection (PZT) of the acoustic waves resulting from the heating of the specimen may be used, a suitable crystal being bonded to a solid specimen before insertion into the chamber 1. Alternatively the bonding may be carried out under UHV conditions within the chamber. However, this technique is not favoured for investigations in production circumstances, as it may impose unacceptable time and handling constraints on the analysis. In certain circumstances, direct physical contact will suffice.

In a second arrangement, detection of the thermal waves may be carried out by a capacitance probe positioned to the rear, or optionally to the front, of the specimen. A probe of this kind will detect the very small thermal expansions and contractions of the rear or front face of the specimen that take place during TWM. This provides non-contact detection of the thermal waves, but very fine positioning of the probe is essential. A probe of this nature requires an associated control system to maintain the position of the probe in the required relativity to the sample. It thus also restricts the shape and nature of the samples which may be examined and hence imposes major constraints at sample level.

In a favoured arrangement, non-contact front-viewing infra-red detection is provided. This type of detection puts no constraints on the sample and the absence of any need for physical contact with the sample allows the probe to be located at a spacing from the sample. Also, it is uniquely sensitive to the thermal properties of the sample, whereas, with PZT detection, the response can also be sensitive to the elastic properties of the sample.

In use of the method of the invention, specimens or samples are introduced into chamber 1, unmounted or ready mounted into SEM type stubs, as appropriate, from atmosphere via the interlock 3. Particularly versatile specimen manipulators are necessary for these tasks and in adaptations of the apparatus for, for example, rapid examination of a succession of specimens in a production context, suitable control systems and techniques may be applied to the manipulators to ensure precise positioning of the specimens during analysis and also while surface portions are undergoing exposure to ion etching or the like, in conjunction with the analysis. Sample sizes for this construction of the apparatus are generally of the order of 10 mm diameter but substantially larger specimens may be accommodated in alternative constructions of the apparatus of the invention.

In a particular experimental methodology applicable to the apparatus of the invention, specimen/PZT assemblies may be introduced into the chamber 1. Where especially aggressive preparation regimes are used, the prepared specimens may be coupled to the transducers within the preparation chamber. The method of specimen/PZT coupling used depends on the specimens being examined and the procedure. Normally, the coupling is achieved either by direct clamping of transducer to specimen or by means of UHV-compatible adhesive. In certain cases, the specimen may be a coating laid down directly onto the transducer itself.

The use of TWM and surface analysis techniques in close association with each other is believed to provide, for the first time in this field of technological investigation, the possibility of undertaking both detection and diagnosis within a single examination, while yet keeping the specimen at all times under UHV, which is essential in order to maintain the cleanliness of the surfaces under study.

A particular advantage of this combination of TWM and surface analysis techniques resides in allowing rapid investigations to be carried out in a production context, where speed of inspection or examination and rapid feed-back is of primary importance. TWM provides the first tool in this situation, for revealing whether flaws or faults exist by looking at the surface and sub-surface conditions. Ion-etching may then be carried out on selected regions where the presence of faults has been indicated by TWM, for the further surface analysis techniques to be applied, thereby enabling the user to examine the flaws and show the reasons for the faults. Thus the apparatus of the invention facilitates not only identification of faults or flaws but also allows their causes to be looked at or studied, all in one sequence of operations or in a simultaneous investigation.

This method of investigation may be applied in an especially effective manner in the electronics industry. A batch of samples can be run through a testing procedure in the apparatus and when an unsatisfactory sample is encountered, it may be explored further by ion etching and chemical analysis to find out why a particular region of the sample has a flaw. Flawed regions may be compared directly within the apparatus with a control region known to be fault-free. Thus detection and diagnosis are accomplished within the compass of one operation and a single apparatus.

Operations may be executed by a user in person, who identifies the regions to be analysed by specific techniques. Alternatively the investigations may be semi-automated, the user identifying the areas to be studied and the apparatus being then programmed to attend to the detailed analysis under the control of, typically, computer means associated with it in a control relationship. In yet another arrangement, the apparatus may form part of a fully automated system in which the identification and location of faults is carried out automatically, and the system of which the apparatus forms a part is programmed to study those locations where faults are identified and report accordingly to a user, either by directly alerting the user or by recording the results of the investigations for subsequent user study.

While the apparatus of FIG. 1 is an entirely acceptable construction in so far as meeting the requirements of the invention is concerned, the space available on the solid angle defined by the wall of the chamber 1 represents a constraint on the number of items which can be mounted on said wall for operating on samples within the chamber or detecting events within it.

Figure 2:
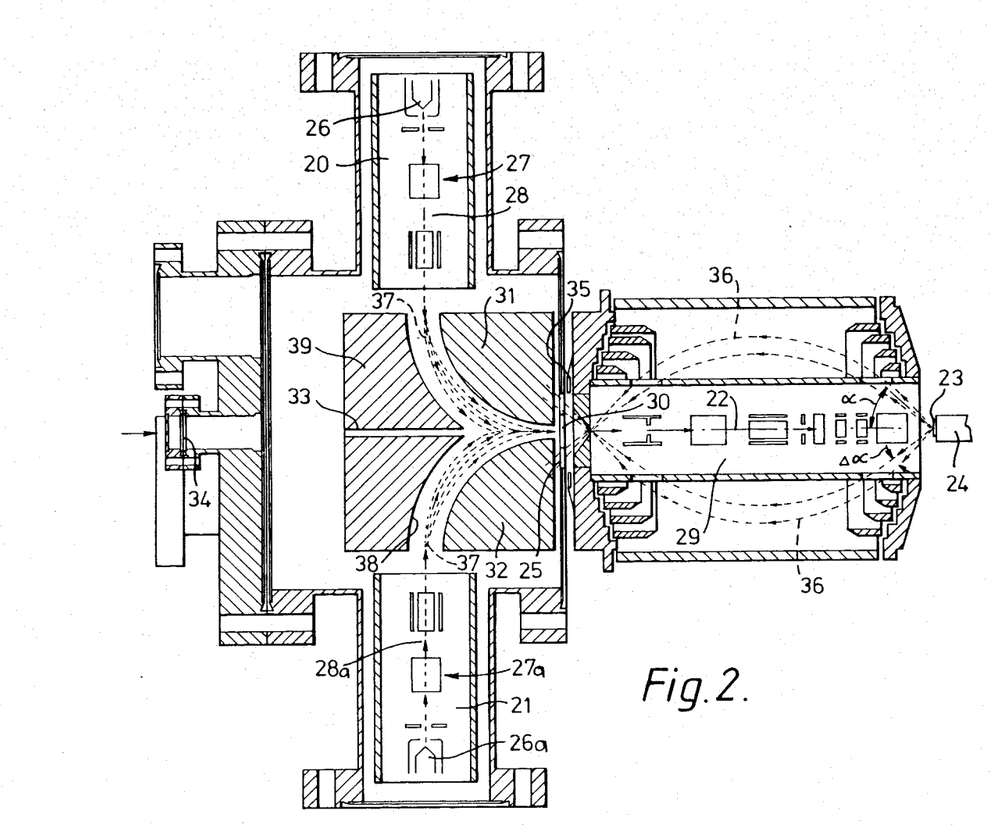
FIG. 2 shows, in axial section, a cylindrical mirror analyser having a primary radiation source in the form of an electron or ion gun and adapted to permit a laser beam to be directed onto a sample positioned in the analytical chamber of apparatus according to the invention.

Accordingly FIG. 2 shows a novel construction of single-pass cylindrical mirror analyser (CMA), which is of particular relevance to the apparatus of the present invention, but is also of general utility in the field of spectroscopic analysis. As shown in this drawing, the CMA incorporates suitable sources of primary radiation, such as electron or ion guns 20 and 21, the radiation from these being directed along the axis 22 of the analyser to a specimen 23 mounted on a support 24. An annular channel plate detector 25 is used to pick up the secondary emission from the specimen 23. The plates of the detector 25, to which a voltage is applied, have a large number of small tubes with lead-doped walls. The impact of electrons against these walls produces a multiplying effect to facilitate detection. With two such plates in a back-to-back configuration, a gain of $10^6$ may be achieved. Variable aperture means 35 is provided for selectively changing the area of the annular channel plate detector exposed to the secondary emission from the specimen 23, which returns to the detector along the paths indicated by references 36. Aperture means 35 is thus located in front of the collector relative to the returning secondary emission.

Each electron or ion gun 20 and 21 is in two parts, the sources 26, 26a, and the input lens, indicated generally by references 27, 27a respectively of the guns being disposed in each case on a respective radial axis 28, 28a relative to the main axis of the analyser, with the output lens, the stigmator and the deflection plates, all indicated generally by reference 29, being located co-axially with said main axis 22. Thus the output lens, the stigmator and the deflection plates are common to each ion or electron gun 20 and 21. The electrons or ions generated in the guns 20 and 21 are in each case deflected and focussed onto the central main axis 22 of the analyser and through the central aperture 30 of the annular channel plate detector 25 by a half-hemisphere 31 or 32 along paths denoted by references 37.

Each half-hemisphere effectively equates to a quarter of a sphere and is spaced from a corresponding concave inwardly directed spheroidal surface 38 of a concave member 39 having a central cusp, so that a space substantially defining a region in space equating to that which would be occupied by a portion of a hollow sphere having a finite wall thickness exists between each said half-hemisphere and its corresponding concave surface. This spherical arrangement serves to focus a parallel electron beam input to the diverter or deflector defined by each half-hemisphere and its associated concave surface from the respective gun 20 or 21 to substantially a single point at the output from the diverter on the central axis of the CMA. For this purpose the half-hemispheres 31 and 32 are positively charged and the concave-surface defining member 39 is negatively charged, while the initial focussing of the electron beams from the guns 20 and 21 is such as to present them to the diverters as parallel beams.

It will be appreciated that the size of the gap between the half-hemispheres and the concave member is significantly exaggerated in the drawing. As an alternative to the half-hemisphere arrangement, a cutaway structure may be used in which the space between the positively and negatively charged members of the diverter represents a space corresponding to a solid sector of a sphere. However in this instance, fringing plates (i.e. electrostatic field corrector or terminator plates) would be needed. By contrast, in the half-hemisphere construction, a uniform field is maintained to a considerable distance to each side of the actual path followed by the electrons.

A cylindrical construction would also be possible, but in such an arrangement, the electron beam would be brought onto a line at the output, rather than the point output of the spherical diverter. This feature of point focussing of the output from the diverter is of considerable value and importance, in that the hole through which the electrons pass into the main cylindrical section of the CMA is also the hole through which electrons return to the channel plate. This hole must be small to meet the requirements of the channel plate detector, and by keeping the input beam to a narrow path, substantially defining a point, the spheroidal diverter also assists in keeping the diametral dimension of this hole to a minimum.

A central axial opening 33 along the main axis 22 of the analyser continues through the concave member beyond the region of said half-hemispheres 31 and 32 to view port 34 at the axial end of the CMA unit remote from the specimen support 24. This central opening 34 allows a laser beam to be directed from a suitable source directly through the CMA along its axis 22 and onto the specimen 23 positioned on the support 24.

A piezo-electric transducer or a capitance probe may be positioned at the rear of the specimen 23. However, if infra-red detection is to be used with this configuration of analyser, a portion of the periphery of the CMA in the region of the specimen mount must be cut away in order to permit viewing access to the front surface of the specimen, a selected surface region of which is heated locally by the laser beam in TWM. Regardless of the detection arrangement for the TWM, this construction of CMA also permits the use of PAS, again within the confines of a single apparatus and one analytical chamber. This versatility of application between these various techniques is also believed to be novel.

In an alternative construction, the electron or ion gun may be disposed on the main axis 22 of the analyser with the laser beam coming in radially along a path at 90° to said main axis. In this instance a mirror is then provided which may be flicked into and out of the axial radiation path along the centre of the analyser to divert the laser beam onto said main axis as required. This construction accordingly represents a partial inversion of the arrangement illustrated.

Figure 2A:
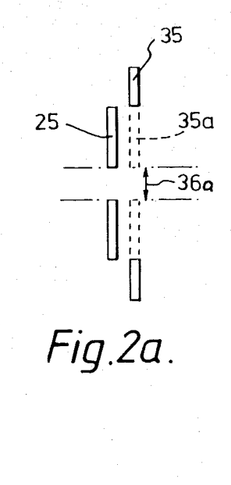
FIG. 2A shows, in enlarged schematic detail, the relationship between the variable aperture means of the analyser of FIG. 2 and the annular channel plate detector of the analyser.

FIG. 2A is an enlargement of the annular channel plate collector and variable aperture region of the analyser of FIG. 2. The aperture means 35 may be of the iris type employed, inter alia, in photographic cameras. The fully open or maximum aperture configuration of means 35 is shown in solid outline, while the minimum aperture configuration of the aperture means is indicated in dotted outline by reference 35a. The diametral extent of the minimum aperture is denoted by reference 36a. This minimum aperture condition corresponds to a clear and unobstructed path remaining for the passage of a laser beam along channel 33 and onwards on the central longitudinal axis of the analyser to sample 23. Thus central channel 33 and its notional linear axial continuation are always open to the laser beam. The aperture means 35 may be controlled from the exterior of the analyser by a suitable linkage.

Figure 3:
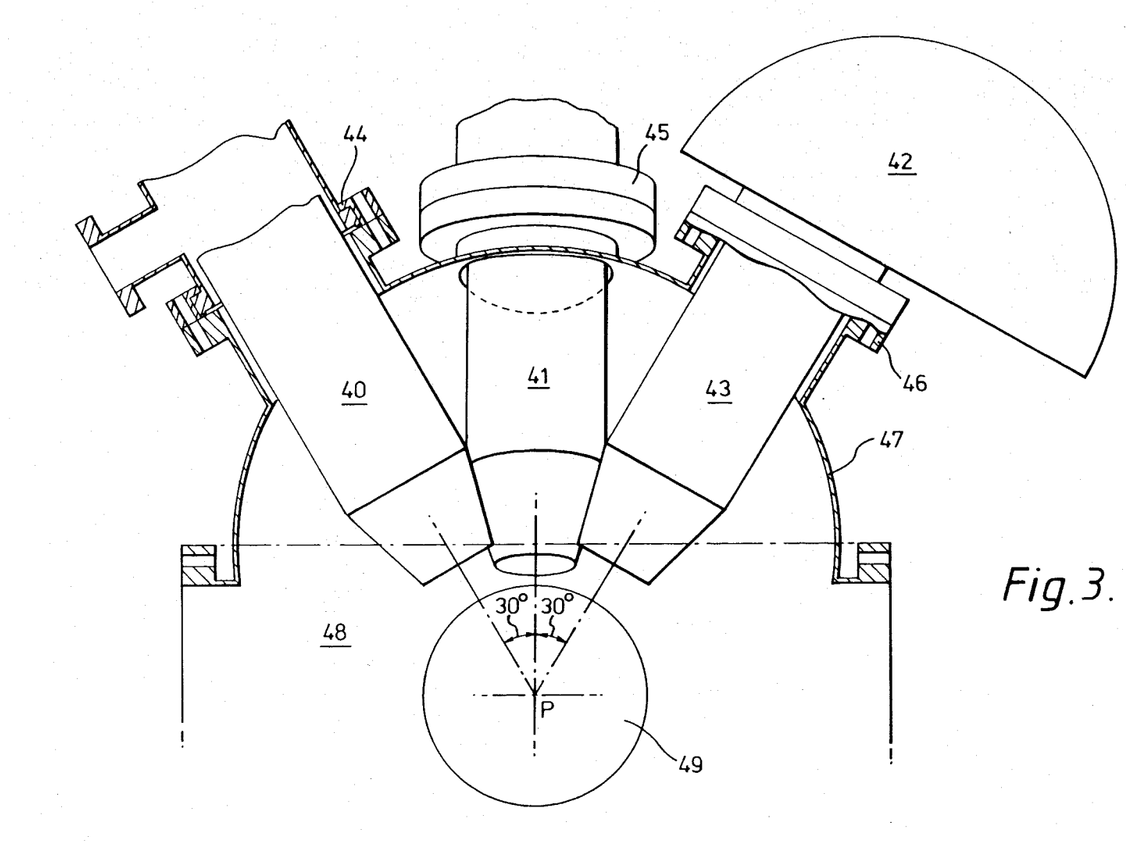
FIG. 3 shows one arrangement for locating an electron gun, a hemispherical detector and an infra-red detector around the wall of a generally spherical analytical chamber in apparatus according to the invention.

The constraint on direct non-contact heat detection by thermal sensors focussing on the heat coming off the sample, arising from geometric considerations, leads to a further construction of apparatus according to the invention, closely resembling the embodiment schematically indicated in FIG. 1, and now illustrated in FIG. 3. In this arrangement, an electron gun 40 or other like probe, an infra-red detector 41 and a hemispherical analyser 42 with input lens 43 are arranged in a cluster around the specimen in ports 44, 45 and 46 of the wall 47 of a substantially spherical chamber 48 of apparatus according to the invention. Thus analysis of the specimen by the various means extending through these narrow-angle ports 44, 45 and 46 is facilitated. In this narrow-angle analysis, a narrow-angle beam from the electron gun 40 may be focussed on a small area of the sample and the infra-red lens 43 is similarly focussed on the signals emitted from this area, while the hemispherical analyser 42 allows narrow-angle analysis of secondary emission in surface analysis techniques.

Hemispherical collectors may be less sensitive than CMAs for certain purposes but they work over a smaller solid angle. They thus offer the primary advantage of freeing a greater working volume around the sample, which may allow more tools to be added in this region, for example including an electron gun of higher resolution. The hemispherical collector may also be used in XPS, which is not practicable with a single-pass CMA, as this does not offer sufficient resolution, XPS requiring a double-pass version of the CMA. Thus the hemispherical analyser may serve for more than one surface analysis technique and affords enhanced versatility so far as adding further features is concerned.

Reference 49 indicates a further port on which a CMA incorporating a gun or laser window in the manner of the FIG. 2 construction may be mounted to also beam down onto a sample positioned appropriately for narrow-angle analysis, thus permitting further techniques to be applied to the sample without necessarily displacing it within the chamber. Thus effectively a dual instrument may be provided within the confines of a single unit, use of the CMA corresponding to a first instrumental use of the apparatus and use of the narrow-angle features equating to a second instrumental use.

Figure 4:
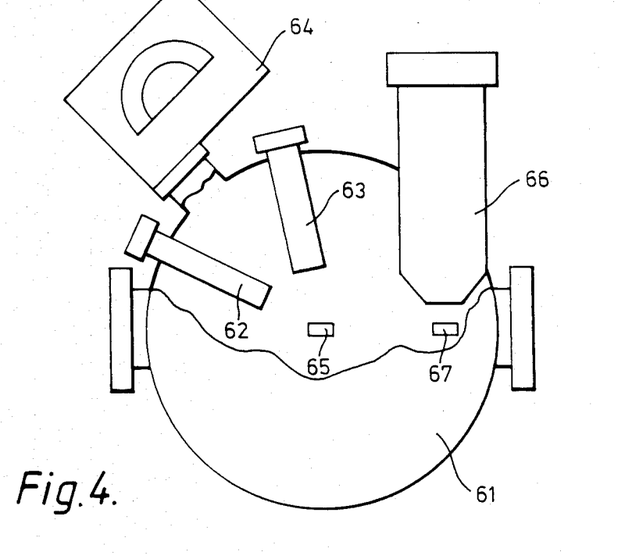
FIG. 4 is a schematic top view on a diametral section of another arrangement of gun and infra-red and hemispherical detectors in a generally spherical analytical chamber of apparatus in accordance with the invention, in which a cylindrical mirror analyser is located in a disposition in which it focusses on a specimen position displaced from that on which the gun and infra-red and hemispherical detectors focus.

A somewhat different construction is shown schematically in the representation of the spherical region 61 of an analyser as depicted in FIG. 4, in which an electron gun 62, an infra-red detector 63 and a hemispherical collector 64 cluster around a sample support position 65 in the same manner as in FIG. 3. However, in this instance, a CMA, indicated at 66, focusses on an alternative sample position 67. The arrangement is somewhat similar to that of FIG. 1, but represents an elevation view of the apparatus from a viewpoint at approximately 90° to that of FIG. 1. Thus simultaneous analyses may be conducted on two samples, one at each position 65 and 67, or alternatively, the same sample may be examined in succession at each of the two positions 65 and 67.

A critical feature of the scanning thermal wave facility is its ability to probe, in a non-destructive manner, the micro-structure and other physical properties of the sub-surfaces of materials. Coupled with surface-sensitive analytical techniques, the apparatus of the invention represents an especially advantageous multi-technique instrument for investigating the physico/chemical characteristics of material surfaces and interfaces and provides a useful addition to the methodologies available to researchers into materials. In addition, the nature of the invention is such that real-world engineering specimens may be handled, since external chemical and mechanical preparation of specimens is not necessary.

A surface analysis system embodying the principles and apparatus of the present invention will now be described having regard to the schematic diagram of FIG. 5. As shown in this drawing, an argon beam supplies unit 81 comprises a supply of argon gas, means for ionising, accelerating and focussing an argon ion beam, and electrostatic beam deflection means. An electron beam supplies unit 82 includes means for generating electron emission from a heated filament or cathode, means for accelerating and focussing an electron beam, and electrostatic beam deflection means. A beam modulator 83 provides an input to electron beam supplies unit 82, and includes means for modulating or chopping the electron beam, which may suitably be achieved by using a control electrode to turn off the beam, or alternatively, a deflection system may be used to sweep the beam across an aperture.

In a beam positioning stage denoted by reference 84, the argon ion beam is located as required for sample analysis by electrostatically positioning it at given sample coordinates. The electron beam is rastered by unit 85, which includes means for electrostatically sweeping or rastering the beam over a given region of the sample.

Reference 86 denotes the sample itself, while sample positioning (87) is achieved by mechanically locating the sample within or at a given region of the UHV system.

References 88, 89 and 90 of the drawing indicate the various detection features of the system, of which the SEM detector may be either a channel electron multiplier collecting a portion of the secondary electrons emitted on excitation of the sample, or the current collected by the sample. The AES detector 89 and the thermal detector 90 have been discussed previously and do not require further specific treatment in connection with the present Figure.

The image computing stage 91 includes a computerised framestore and memory system, along with facilities for image processing.

Inputs to the computing means 91 are received from the detector stages, 88 to 90 as appropriate, while item 91 itself also supplies a feedback signal to the beam positioning stage 84. A forward output from the computing stage 91 provides an input to an image displays stage 92, which includes black and white and colour video monitors. A further input to the image displays stage comes directly from the beam raster stage 85, while a two-way communication link exists between the displays unit 92 and a user interface stage 93, providing interactive user aids for the system.

Figure 5:
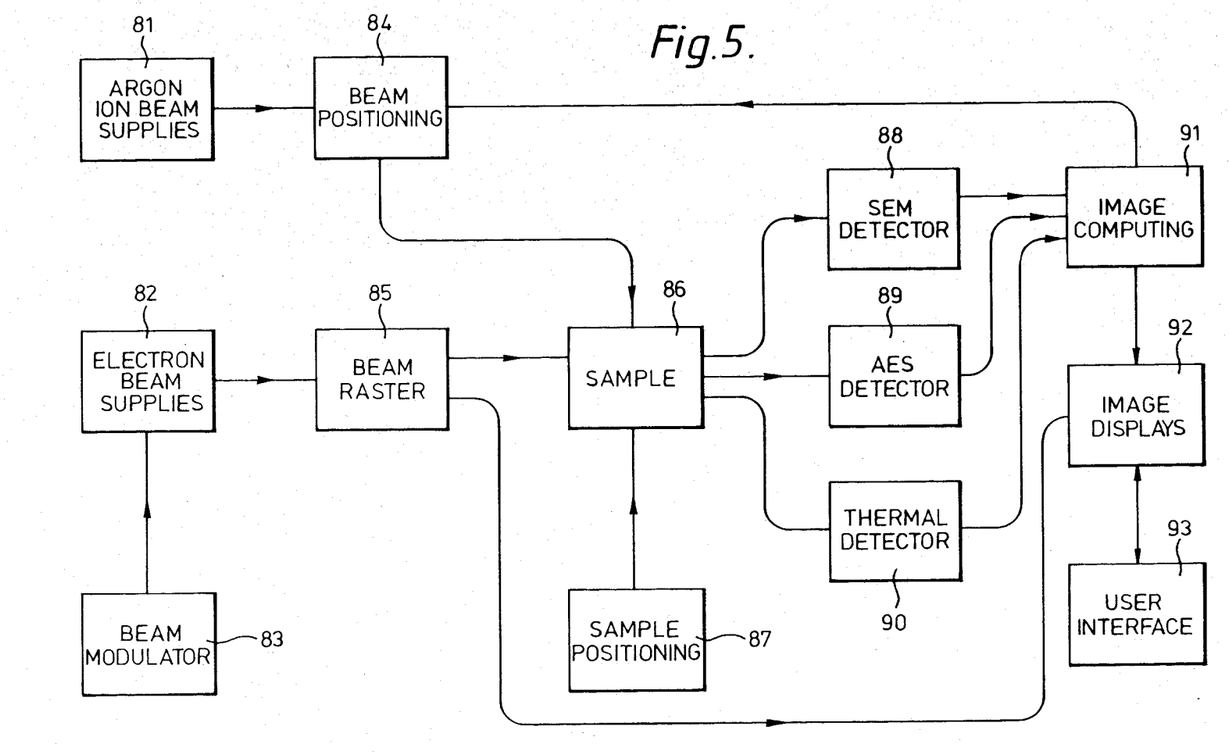
FIG. 5 is a schematic block diagram of a surface analysis microscopy system according to the invention and incorporating the apparatus of the invention.

Operation of the system depicted schematically in FIG. 5 is as follows. The sample 86 is positioned by means 87 so that the appropriate portion of the sample resides within the scan field of the electron and ion beams. The electron beam is then activated using supplies means 82 and raster unit 85. During this process, the SEM image, established by use of detector 88, image computing stage 91 and image displays unit 92, is used to observe the sample surface. Sub-surface defects are located using the thermal image path denoted by the sequence 90, 91 and 92 of FIG. 5.

The coordinates of any sub-surface defects encountered are then noted together with the coordinates of defect-free regions of the sample 86. This noting or coordinate recordal may be carried out by computer means of the system. The coordinates of the defects are then used to target the scanning Auger image, denoted by path 89, 91 and 92, and the argon ion etching, carried out by units 81 and 84.

The interactions between these various techniques are determined by the user at location 93 of FIG. 5, either interactively or by programming the image computer 91 to recognise certain features and initiate certain further actions in dependence on the identification of the presence of such features.

Thus in carrying out an analysis according to the invention, a specimen is loaded through the interlocks into the ultra-high vacuum environment within the chamber and scanned using, for example, the SEM and TWM technique. If all is in order, as revealed by this technique, the specimen may then again pass out of the chamber. If however, a fault is found to be present, others of the various techniques provided in the apparatus and system of the invention may be deployed to locate the problem and determine its nature. The system may be automated so that if an apparent imperfection is detected, then the computer means of the system notes the coordinates where the anomaly was detected and activates an appropriate further technique to investigate the anomaly further. Thus the method and system of the invention are especially suited to monitoring surface and sub-surface quality in a production situation, where a succession of samples may be examined one after the other in the UHV chamber on a more or less production line basis.

Figure 6:
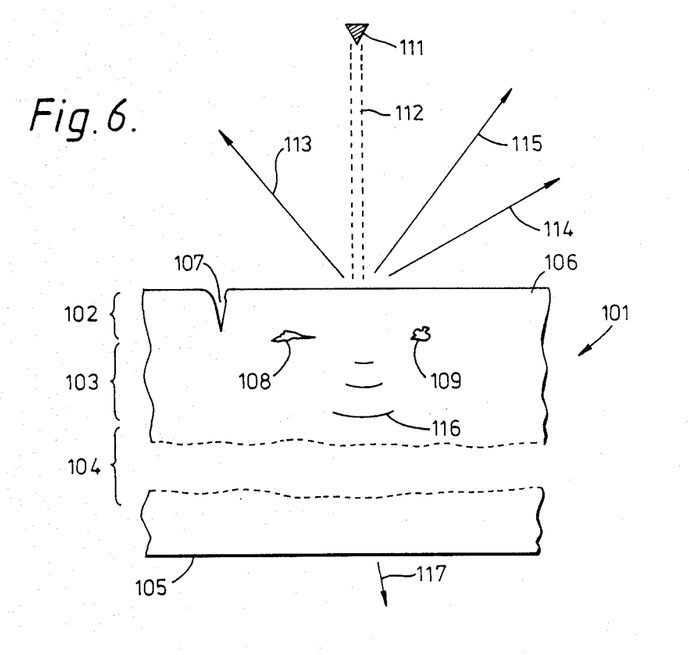
FIG. 6 is a diagrammatic representation of a typical analytical situation in which the apparatus, method and system of the invention are applied to the examination and analysis of a sample of material.

FIG. 6 is a schematic representation of a typical situation to which the apparatus, method and system of the present invention are especially suited. A sample 101 has a surface layer or region 102 which may be only two or three atoms thick. Underlying the surface portion 102 is a sub-surface region 103 which may be between ten and twenty atoms deep, or which may extend to several mm, depending on the nature of the material of the sample. Underlying the sub-surface region is the bulk material portion or region 104 of the sample. A finite sample will necessarily have a further face region 105, remote from the surface 102 under study, but this is not relevant to the present invention, other than in respect of certain signal detection techniques. The surface 102 may, depending on the particular sample, also have a coating or lamination 106 applied to it, study or investigation of which may also be required.

Typical sample imperfections depicted schematically in FIG. 6 include a surface crack 107, a sub-surface void 108 and a sub-surface inclusion 109.

Reference 111 denotes a scanned and chopped electron beam source from which a beam 112 is directed onto the sample surface 102. SEM signal detection is indicated schematically by reference 113, the AES signal by 114, and infra-red thermal microscopy detection (TWM) by reference 115. Reference 116 indicates the acoustically carried thermal signals which propagate through the sample towards its opposite face 105, where thermal detection may take place by piezo-electric or capacitance means indicated schematically by reference 117, as an alternative to the infra-red detection denoted schematically at 115.

The following information may be obtained in a single study or analysis:
(a) via SEM : an image of surface topography,
(b) via TWM : the location of sub-surface defects,
(c) via AES : the chemistry of the surface, and
(d) via AES and argon etching targeted by TWM : the chemistry of sub-surface defects and that of control regions of the same sample.

In a further brief enlargement of the thermal microscopy aspect of the analysis, when the chopped or modulated energy beam is applied to the sample or specimen, the temperature of the sample is raised locally in the vicinity of the point of impingement of the beam, and this heating is monitored to provide information about the sample. The heating phenomenon resulting from the pulsed energy input may be explained, as already discussed, in terms of thermal waves, the thermal waves leading to generation of acoustic waves by virtue of the cyclic expansion and contraction of the heated region of the material of the region of the sample to which the energy input is applied. While the thermal waves themselves are affected by the presence of defects or discontinuities in the material and thus provide information about the structure of the sample, the wavelength of the acoustic waves is much greater, so that these waves do not, as it were, "see" the imperfections, and travel through the material without being affected by them. Thus the acoustic waves serves to pass information about the imperfections detected by the thermal microscopy to detection means of the system of the invention. The detection means may be, for example, a piezo-electric probe located at a rear face of the sample, or a capacitance probe in the same region, the spacing of which is controlled to remain fixed relative to the sample during expansion and contraction of the material of the sample, the resulting controlling movements then providing an output from the system. With this form of detection, the bulk material portion of the sample serves merely as a transmission medium for the acoustic signals.

Alternatively, the thermal effects may be monitored directly by infra-red ray means focussed on the energised area of the sample, to detect temperature variations in this region. Since the heat input of the pulsed beam is relatively small, there are advantages in working at higher overall sample temperatures, since infra-red emission increases rapidly with higher source temperatures, subject to the necessary constraint that UHV conditions must be maintained at all times around the sample.

What is claimed is:

1. Surface analysis apparatus comprising:
(a) a substantially hermetically sealable chamber;
(b) means for establishing an ultra-high vacuum environment in said chamber;
(c) means for supporting a test specimen within said chamber when ultra-high vacuum conditions prevail therein;
(d) a plurality of means for directing a beam at said test specimen for transfer of energy thereto, at least one of said plurality of beam-directing means adapted to direct a beam at a selected surface region of said test specimen for transfer of energy to said selected surface region;
(e) means for detecting emissions from said test specimen when excited by energy transfer thereto, said emissions detecting means including means for establishing the temperature of said selected surface region when excited by energy transfer to said selected surface region from said beam of said at least one of said plurality of beam-directing means; and
(f) means for analysing said emissions to provide data indicative of at least surface properties of said test specimen.

2. Apparatus according to claim 1, wherein said at least one of said plurality of beam-directing means includes means for modulating the intensity of said beam of said at least one of said plurality of beam-directing means.

3. Apparatus according to claim 1, wherein means are provided for focussing said beam of said at least one of said plurality of beam-directing means onto said selected surface region.

4. Apparatus according to claim 1, wherein means are provided for scanning or rastering said beam of said at least one of said plurality of beam-directing means relative to the surface of said test specimen in accordance with a predetermined pattern.

5. Apparatus according to claim 1, wherein said means for establishing the temperature of said selected surface region to which energy is transferred by the directing of said beam of said at least one of said plurality of beam-directing means thereonto includes an infra-red detector for sensing the heat emission from said selected surface region.

6. Apparatus according to claim 1, wherein said chamber has a generally spherical region, said region having a number of narrow-angle ports, so that at least an infra-red thermal emission detector and a concentric hemispherical analyser may be mounted on said ports to substantially cluster about a specimen position.

7. Apparatus according to claim 1, wherein said means for supporting a test specimen within said chamber is adapted to support a test specimen at a plurality of specimen positions within said chamber; said chamber having a generally spherical region, and said region having a plurality of narrow-angle ports; the apparatus comprising an infra-red thermal emission detector mounted on one of said plurality of narrow-angle ports for detection of emission from a test specimen located at a first specimen position of said plurality of specimen positions and a concentric hemispherical analyser mounted on another of said plurality of narrow-angle ports for detection of emission from a test specimen located at said first specimen location; said chamber also having a further port, and the apparatus comprising a cylindrical mirror analyser mounted on said further port for detection of emission from a test specimen located at a second specimen position of said plurality of specimen positions, said first and second specimen positions spaced apart within said chamber, and the apparatus also comprising means for transferring a test specimen between said first and second specimen positions.

8. Apparatus according to claim 1, comprising means for introducing a test specimen into said chamber when ultra-high vacuum conditions prevail therein.

9. A surface analysis system comprising apparatus according to claim 1, together with computer means for processing data from said detecting means to provide output information of the system.

10. A surface analysis system according to claim 9, wherein means are provided for scanning or rastering said beam of said at least one of said plurality of beam-directing means relative to the surface of said test specimen in accordance with a predetermined pattern and said computer means correlates data from said detecting means with said scanning or rastering of the beam.

11. A surface analysis system according to claim 9, wherein said computer means controls said plurality of beam-directing means to activate selected ones of said plurality of beam-directing means in dependence on the presence of certain predetermined characteristics in said emissions from said selected surface region.

12. A surface analysis method comprising the steps of:
 (a) supporting a test specimen within a substantially hermetically sealable chamber when ultra-high vacuum conditions prevail thereon;
 (b) directing a beam at a selected surface region of said test specimen for transfer of energy to said selected surface region;
 (c) detecting emissions from said selected surface region when excited by energy transfer thereto;
 (d) analysing said emissions to provide data indicative of at least surface properties of said test specimen, said emission-detecting step including establishing the temperature of said selected surface region;
 (e) directing a further beam at said test specimen in dependence on information about the test specimen disclosed by said emissions analysis; and
 (f) detecting and analysing further emissions from said test specimen resulting from the directing of said further beam thereat.

13. A method according to claim 12, wherein said beam is modulated to apply a pulsed chopped intensity-modulated energy input to said selected surface region.

14. A cylindrical mirror analyser comprising at least one source of primary radiation for initiating a primary radiation beam, means for focussing said primary radiation beam substantially at a specimen position located substantially on the longitudinal axis of the analyser, port means for admission of a beam from a beam source to the analyser, and means for permitting said beam from said beam source to be focussed substantially at said specimen position, wherein at least one of said at least one source of primary radiation and said port means is disposed so that a beam passing through the analyser from said at least one of said at least one source of primary radiation and said port means is initially directed along a radial axis extending at substantially 90° to said longitudinal axis, and the analyser also comprises means for diverting said beam from said radial axis onto said longitudinal axis for focussing substantially at said specimen position.

15. A cylindrical mirror analyser according to claim 14, wherein said at least one source of primary radiation is disposed to initially direct said primary radiation beam along said radial axis extending at substantially 90° to said longitudinal axis of the analyser, and said beam diverting means is adapted to divert said primary radiation beam onto said longitudinal axis for focussing substantially at said specimen position.

16. A cylindrical mirror analyser according to claim 14, wherein said at least one source of primary radiation is disposed to initially direct said primary radiation beam along said longitudinal axis, and said port means is disposed for admission of said beam from said beam source for initial direction of said beam along said radial axis, and said beam diverting means is adapted to selectively divert said beam from said beam source substantially onto said longitudinal axis.

17. A cylindrical mirror analyser according to claim 14, wherein said means for permitting said beam from said beam source to be focussed substantially at said specimen position includes a passage extending within the analyser from said port means in the direction of said specimen position.

18. A cylindrical mirror analyser according to claim 17, wherein said specimen position is located substantially at one axial end of the analyser, said port means is located substantially at the other axial end of the analyser, and said passage extends along the axis of the analyser.

19. Surface analysis apparatus comprising:
 (a) a substantially hermetically sealable chamber having at least one port;
 (b) means for establishing an ultra-high vacuum environment in said chamber;
 (c) means for supporting a test specimen within said chamber when ultra-high vacuum conditions prevail therein;

(d) a plurality of means for directing a beam at said test specimen for transfer of energy thereto, at least one of said plurality of beam-directing means adapted to direct a beam at a selected surface region of said test specimen for transfer of energy to said selected surface region;

(e) means for detecting emissions from said test specimen when excited by said energy transfer thereto, said emissions detecting means including means for establishing the temperature of said selected surface region when excited by energy transfer to said selected surface region from said beam of said at least one of said plurality of beam-directing means and said emissions detecting means also including a cylindrical mirror anmalyser mounted on said at least one port for detecting emissions from said test specimen; and (f) means for analysing said emissions to provide data indicative of at least surface properties of said test specimen.

* * * * *